(12) United States Patent
Saitoh et al.

(10) Patent No.: US 8,338,149 B2
(45) Date of Patent: Dec. 25, 2012

(54) ETHANOL PRODUCTION PROCESS AND YEAST FOR ETHANOL PRODUCTION

(75) Inventors: Satoshi Saitoh, Nissin (JP); Kazushi Takahashi, Nagoya (JP); Kayo Miyata, Toyota (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 351 days.

(21) Appl. No.: 12/745,453

(22) PCT Filed: Nov. 21, 2008

(86) PCT No.: PCT/JP2008/071191
§ 371 (c)(1),
(2), (4) Date: Jun. 17, 2010

(87) PCT Pub. No.: WO2009/069538
PCT Pub. Date: Jun. 4, 2009

(65) Prior Publication Data
US 2011/0250665 A1     Oct. 13, 2011

(30) Foreign Application Priority Data
Nov. 30, 2007   (JP) ................ 2007-310870

(51) Int. Cl.
*C12P 7/06*     (2006.01)
(52) U.S. Cl. ..................................... 435/161
(58) Field of Classification Search ............... None
See application file for complete search history.

(56) References Cited

U.S. PATENT DOCUMENTS

| 4,472,501 A | 9/1984 | Takasawa et al. |
| 4,472,801 A | 9/1984 | Huang |
| 5,100,791 A | 3/1992 | Spindler et al. |
| 6,102,690 A | 8/2000 | Ingram et al. |
| 7,344,876 B2 | 3/2008 | Levine |

FOREIGN PATENT DOCUMENTS

| JP | 05-207885 A | 8/1993 |
| JP | 2001519662 A | 10/2001 |

OTHER PUBLICATIONS

*Aspergillus oryzae* (Ahlburd) Cohn var. Brunneus Murakami, National Institute of Technology and Evaluation, NBRC No. 4278, NITE Biological Resource Center, Reference Detail Information, retrieved from the Internet: http://www.nbrc.nite.go on Jan 26, 2012.
Gabor Peter et al.: "Six new methanol assimilating yeast species from wood material", Antonie van Leeuwenhoek, Kluwer Academic Publishers, vol. 84, No. 2, pp. 147-159, 2003.
List of Cultures 2000 Microorganisms, Eleventh Edition, Jan. 31, 2001, pp. 72-74.
Samaniya Sukroongreung et al: "Survey of Sensitivity of Twelve Yeast Genera Toward T-2 Toxin", Applied and Environmental Microbiology, 1984, vol. 48, No. 2, pp. 416-419.

Yuka Nagatsuka et al: "*Ogataea neopini* sp. nov. and *O. corticis* sp. nov., with the emendation of the ascomycete yeast genus *Ogataea*, and transfer of *Pichia zsoltii*, *P. dorogensis*, and *P. trehaloabstinens* to it", The Journal of General and Applied Microbiology, vol. 54, No. 6, Dec. 2008, pp. 353-365 (2008).
Villa-Carvajal, Mercedes, et al., "Identification of species in the genus *Pichia* by restriction of the internal transcribed spacers (ITS1 and ITS2) and the 5.8S ribosomal DNA gene," Antonie Van Leeuwenhoek Kluwer Academic Publishers, Aug. 11, 2006, pp. 171-181, vol. 90, No. 2.
Ryabova, Olena B., et al., "Xylose and cellobiose fermentation to ethanol by the thermotolerant methylotrophic yeast *Hansenula polymorpha*," FEMS Yeast Research, Nov. 2003, pp. 157-164, vol. 4, No. 2.
V. Cavazzoni, et al., "Cellobiose Fermentation by Immobilized Cells of Some Yeasts," Annali di Microbiologia ed Enzimologia, 1987, pp. 127-133, vol. 37, No. 2.
*Pichia* glucozyma., [online], DSMZ, [Retrieved on Dec. 5, 2008], Retrieved from the internet:URL:http://www.dsmz.de/microorganisms/bacteria_info.php?id species=779592 , 1 page total.
NBRC 101078., [online], NITE Biological Resource Center, Catalogue Detail Information.,[Retrieved on Dec. 5, 2008]., Retrieved from the internet:URL:http://www.nbrc.nite.go.jp/NBRCZ , 1 page total.
ATCC 76276, [online], ATCC The Global Bioresource Center, Product Description., [Retrieved on Dec. 5, 2008], Retrieved from the internet:      <URL:       http://www.atcc.org/ATCCAdvancedCatalogSearch/ProductDetails.tabid/452/Default.aspx> 2 pages total.
ATCC 18938, [online], ATCC The Global Bioresource Center, Product Description, [Retrieved on Dec. 5, 2008], Retrieved from the internet:URL:http://www.atcc.org/ATCCAdvancedCatalogSearch/ProductDetails/tabid/452/Default.aspx , 2 pages total.
ATCC, 28781, [online], ATCC The Global Bioresource Center, Product Description.,[Retrieved on Dec. 5, 2008]., Retrieved from the interenet:URL:http://www.atcc.org/ATCCAdvancedCatalogSearch/ProductDetails/tabid/452/Default.aspx, 2 pages total.
NBRC 1794, [online], NITE Biological Resource Center, Catalogue Detail Information, [Retrieved on Dec. 8, 2008], Retrieved from the Internet:URL:http://www.nbrc.nite.go.jp/NBRC2/NBRCCatalogueDetailServlet?ID=NBRC&CAT=00001794 1 page total.
Y. Fujita, et al., "Synergistic Saccharification, and Direct Fermentation to Ethanol, of Amorphous Cellulose by Use of an Engineered Yeast Strain Codisplaying Three Types of Cellulolytic Enzyme," Applied and Environmental Microbiology, 2004, pp. 1207-1212, vol. 70, No. 2.
S. Parekh, et al., "Fermentation of Cellobiose and Wood Sugars to Ethanol by *Candida* Shehatae and *Pichia stipitis*.," Biotechnology Letters, 1986, pp. 597-600, vol. 8, No. 8.
A. Toivola, "Alcoholic Fermentation of D-Xylose by Yeasts.," Applied and Environmental Microbiology, 1984, pp. 1221-1223, vol. 47, No. 6.

*Primary Examiner* — Suzanne M Noakes
*Assistant Examiner* — Jae W Lee
(74) *Attorney, Agent, or Firm* — Sughrue Mion, PLLC

(57) ABSTRACT

According to the present invention, ethanol production is carried out with the use of cellulose or cellobiose as a starting material at low cost. The method of the present invention comprises the steps of culturing a microorganism that is classified as a species selected from the group consisting of *Ogataea dorogensis*, *Ogataea pini*, *Ogataea glucozyma*, *Ogataea neopini*, and *Ogataea corticis* in a medium containing cellobiose; and collecting ethanol from the medium.

5 Claims, 1 Drawing Sheet

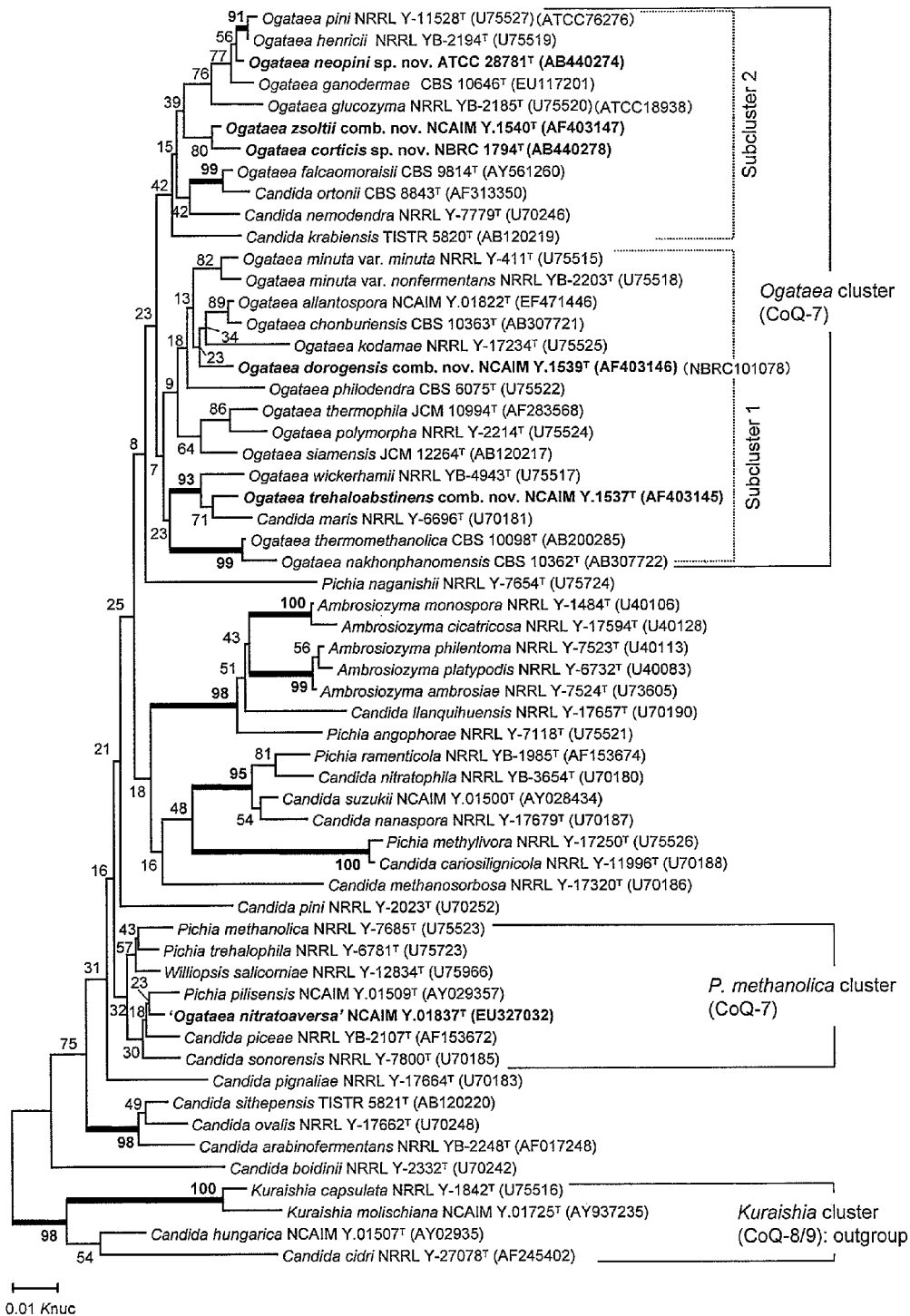

US 8,338,149 B2

SEQUENCE LISTING

```
<160> NUMBER OF SEQ ID NOS: 9

<210> SEQ ID NO 1
<211> LENGTH: 608
<212> TYPE: DNA
```

<213> ORGANISM: Pichia pini ATCC76276

<400> SEQUENCE: 1

| | | | | | |
|---|---|---|---|---|---|
| gcatatcaat | aagcggagga | aaagaaacca | acagggattg | ccttagtagc | ggcgagtgaa | 60
| gcggcaagag | ctcaaatttg | aaatctggta | ccttcggtgc | ccgagttgta | atttgaagaa | 120
| agctgtcttg | gagttggcct | tgtctatgt | tccttggaac | aggacgtcac | agagggtgag | 180
| aatcccgtgc | gatgaagtgt | ccaattcttt | ataagacgtt | ttcgaagagt | cgagttgttt | 240
| gggaatgcag | ctcaaagtgg | gtggtaaatt | ccatctaaag | ctaaatattg | gcgagagacc | 300
| gatagcgaac | aagtactgtg | aaggaaagat | gaaaagaact | ttgaaaagag | agtgaaaaag | 360
| tacgtgaaat | tgttgaaagg | gaagggtatt | caatcagact | tggtatttag | ttatcattac | 420
| tccttgtggg | tggtgctcta | gcttttact | gggccagcat | cagttttggt | ggcaagataa | 480
| tggcagttga | atgtagctcc | tagagtatta | tagcttctgc | tgatattgcc | tactgagact | 540
| gaggtctgcg | gcttttgcct | aggatgctgg | cgtaatgatt | gaataccgcc | cgtcttgaaa | 600
| cacggacc | | | | | 608

<210> SEQ ID NO 2
<211> LENGTH: 607
<212> TYPE: DNA
<213> ORGANISM: Pichia pini ATCC28781

<400> SEQUENCE: 2

| | | | | | |
|---|---|---|---|---|---|
| gcatatcaat | aagcggagga | aaagaaacca | acagggattg | ccttagtagc | ggcgagtgaa | 60
| gcggcaagag | ctcaaatttg | aaatctggta | ccttcggtgc | ccgagttgta | atttgaagaa | 120
| agctgtcttg | gagttggcct | tgtctatgt | tccttggaac | aggacgtcac | agagggtgag | 180
| aatcccgtgc | gatgaggtgt | ccaattcttt | ataagacgtt | ttcgaagagt | cgagttgttt | 240
| gggaatgcag | ctcaaagtgg | gtggtaaatt | ccatctaaag | ctaaatattg | gcgagagacc | 300
| gatagcgaac | aagtactgtg | aaggaaagat | gaaaagaact | ttgaaaagag | agtgaaaaag | 360
| tacgtgaaat | tgttgaaagg | gaagggtatt | caatcagact | tggtatttag | ttatcattac | 420
| tccttgtggg | tggtgctcta | gcttttact | gggccagcat | cagttttggt | ggcaagataa | 480
| tcgcagttga | atgtagctcc | tagagtatta | tagcttctgt | tgatattgcc | tactgagact | 540
| gaggtctgcg | gctttgccta | ggatgctggc | gtaatgatt | aataccgccc | gtcttgaaac | 600
| acggacc | | | | | | 607

<210> SEQ ID NO 3
<211> LENGTH: 609
<212> TYPE: DNA
<213> ORGANISM: Pichia pini NBRC1794

<400> SEQUENCE: 3

| | | | | | |
|---|---|---|---|---|---|
| gcatatcaat | aagcggagga | aaagaaacca | acagggattg | ccttagtagc | ggcgagtgaa | 60
| gcggcaagag | ctcaaatttg | aaatctggta | ccttcggtgc | ccgagttgta | atttgaagaa | 120
| agctgtcttg | aatttggcct | tgtctatgt | tccttggaac | aggacgtcac | agagggtgag | 180
| aatcccgtgc | gatgaggtgt | ccattttcat | ataagacgtt | ttcgaagagt | cgagttgttt | 240
| gggaatgcag | ctcaaagtgg | gtggtaaatt | ccatctaaag | ctaaatattg | gcgagagacc | 300
| gatagcgaac | aagtactgtg | aaggaaagat | gaaaagaact | ttgaaaagag | agtgaaaaag | 360
| tacgtgaaat | tgttgaaagg | gaagggtatt | cgatcagact | tggtatttag | ttatcatcgc | 420
| tccttgtggg | tggtgctcta | acttttact | gggccagcat | cagttttggt | ggcaagataa | 480

```
tggcagttga atgtagctcc ttggagtatt atagcttctg ctgatattgc ctactgggac    540
tgaggtctgc ggcttttgcc taggatgctg gcgtaatgat cgaataccgc ccgtcttgaa    600
acacggacc                                                            609
```

<210> SEQ ID NO 4
<211> LENGTH: 568
<212> TYPE: DNA
<213> ORGANISM: Pichia glucozyma ATCC18938

<400> SEQUENCE: 4

```
aaaccaacag ggattgcctt agtagcggcg agtgaagcgg caagagctca aatttgaaat     60
ctggtacctt cggtgcccga gttgtaattt gaagaaagct gtcttggaat tggcctttgt    120
ctatgttcct tggaacagga cgtcacagag ggtgagaatc ccgtgcgatg aggtgtccaa    180
ttccgtttaa gacgttttcg aagagtcgag ttgtttggga atgcagctct aagtgggtgg    240
taaattccat ctaaagctaa atattggcga gagaccgata gcgaacaagt actgtgaagg    300
aaagatgaaa agaactttga aaagagagtg aaaaagtacg tgaaattgtt gaagggaag     360 ggtattcaat cagacttggt tttaagttat cattactcct tgtgggtggt gctctagctt    420
tttactgggc cagcatcagt tttggtggca agataataac agttgaatgt atctcctttt    480
ggagtgttat agcttctgtt gatattgcct actgagactg aggtctgcgg cttttgccta    540
ggatgctggc gtaatgattg aataccgc                                       568
```

<210> SEQ ID NO 5
<211> LENGTH: 554
<212> TYPE: DNA
<213> ORGANISM: Pichia dorogensis NBRC101078

<400> SEQUENCE: 5

```
aaaccaacag ggattgcctt agtagcggcg agtgaagcgg caagagctca aatttgaaat     60
ctggtacctt cggtgcccga gttgtaattt gaagaaagca atcttggatt tggcctttgt    120
ctatgttcct tggaacagga cgtccataag ggtgagaatc ccgtctgatg aggtgtccat    180
ttctatgtaa gatgttttcg aagagtcgag ttgtttggga atgcagctct aagtgggtgg    240
taaattccat ctaaagctaa atattggcga gagaccgata gcgaacaagt actgtgaagg    300
aaagatgaaa agaactttga aaagagagtg aaaaagtacg tgaaattgtt gaagggaag     360 ggtattagat cagacttggt atttagttat cattactcct tgtgggtggt gctctagctt    420
tttactgggc cagcatcagt tttggtggca agataatgac tgttgaatgt agctcctcgg    480
agtattatag cttcggttga tattgcctac tgggactgag gtctgcggct tttgcctagg    540
atgctggcgt aatg                                                      554
```

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6

```
gcatatcaat aagcggagga aaag                                            24
```

<210> SEQ ID NO 7
<211> LENGTH: 26
<212> TYPE: DNA
<213> ORGANISM: Artificial Sequence
<220> FEATURE:

```
<223> OTHER INFORMATION: Synthetic oligonucleotide

<400> SEQUENCE: 7
ctctcttttc aaagttcttt tcatct                                      26

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
agatgaaaag aactttgaaa agagag                                      26

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
ggtccgtgtt tcaagacgg                                              19
```

ETHANOL PRODUCTION PROCESS AND YEAST FOR ETHANOL PRODUCTION

TECHNICAL FIELD

The present invention relates to an ethanol production process using, for example, a woody biomass. Further, the present invention relates to a yeast for ethanol production, which can produce ethanol from cellobiose used as a carbon source.

BACKGROUND ART

So-called biomass ethanol, which is obtained by producing ethanol by a fermentation method from a biomass used as a starting material, has been gaining attention in view of carbon neutrality. Herein, the term "biomass" is defined as referring to renewable and biological organic resources except for fossil resources. In particular, a woody biomass has been also used as a starting material for ethanol production. Representative examples of a woody biomass include rice straw, rice husks, food waste, livestock excretion, woodchips, firewood, wood charcoal, chips, pellets, briquettes, lumbar chips, sawdust, tree bark, and construction debris.

A woody biomass mainly contains cellulose as a carbon source. When ethanol production is carried out using a woody biomass as a starting material, cellulose is first saccharified with cellobiohydrolase such that cellobiose, which is a disaccharide, is obtained. *Saccharomyces cerevisiae*, which is generally used for ethanol production by a fermentation method, cannot directly produce cellobiose. Therefore, glucose obtained by degrading cellobiose with β-glucosidase is used for fermentation. Specifically, conventional ethanol production with the use of a woody biomass requires a two-stage saccharification step in which cellulose is first formed into cellobiose and then cellobiose is formed into glucose. Accordingly, ethanol production with the use of a biomass containing cellulose, such as a woody biomass, is more costly than ethanol production using a different biomass, and further it comprises complicated production steps.

DISCLOSURE OF THE INVENTION

Problem to be Solved by the Invention

As described above, ethanol production with the use of cellulose or cellobiose as a starting material essentially involves a plurality of enzyme reactions. Therefore, an enzyme reagent or an enzyme reaction system must be used for such production, resulting in high production costs, which has been problematic. Therefore, in view of the above circumstances, it is an object of the present invention to provide an ethanol production process and a yeast for ethanol production that allow ethanol production to be carried out with the use of cellulose or cellobiose as a starting material at low cost.

Means for Solving Problem

As a result of intensive studies in order to achieve the above object, the present inventors have found that ethanol can be synthesized by a specific yeast with the use of cellobiose as a substrate. This has led to the completion of the present invention. Specifically, the present invention encompasses the following.

(1) An ethanol production process, comprising the steps of:
culturing a microorganism that is classified as a species selected from the group consisting of *Ogataea dorogensis*, *Ogataea pini*, *Ogataea glucozyma*, *Ogataea neopini*, and *Ogataea corticis* in a medium containing cellobiose; and
collecting ethanol from the medium.

(2) An ethanol production process comprising the steps of
culturing a microorganism having 26s rDNA-D1/D2 comprising a nucleotide sequence having at least 97% homology with the nucleotide sequence of 26s rDNA-D1/D2 derived from at least one strain selected from the group consisting of the *Ogataea dorogensis* NBRC101078 strain, the *Ogataea pini* ATCC76276 strain, the *Ogataea glucozyma* ATCC18938 strain, the *Ogataea neopini* ATCC28781 strain, and the *Ogataea corticis* NBRC1794 strain in a medium containing cellobiose; and
collecting ethanol from the medium.

(3) The ethanol production process according to (1) or (2), wherein the microorganism is a microorganism that is classified as at least one strain selected from the group consisting of the *Ogataea dorogensis* NBRC101078 strain, the *Ogataea pini* ATCC76276 strain, the *Ogataea glucozyma* ATCC18938 strain, the *Ogataea neopini* ATCC28781 strain, and the *Ogataea corticis* NBRC1794 strain.

(4) The ethanol production process according to (1) or (2), wherein the cellobiose is derived from cellulose contained in a woody biomass.

(5) The ethanol production process according to (4), which further comprises a step of degrading the cellulose contained in a woody biomass into cellobiohydrolase.

(6) The ethanol production process according to (1) or (2), wherein the microorganism has the ability to assimilate cellobiose.

(7) The ethanol production process according to (6), wherein the microorganism further has the ability to assimilate xylose.

(8) A yeast for ethanol production comprising a microorganism that is classified as a species selected from the group consisting of *Ogataea dorogensis*, *Ogataea pini*, *Ogataea glucozyma*, *Ogataea neopini*, and *Ogataea corticis*.

(9) A yeast for ethanol production, which has 26s rDNA-D1/D2 comprising a nucleotide sequence having at least 97% homology with the nucleotide sequence of 26s rDNA-D1/D2 derived from at least one strain selected from the group consisting of the *Ogataea dorogensis* NBRC101078 strain, the *Ogataea pini* ATCC76276 strain, the *Ogataea glucozyma* ATCC18938 strain, the *Ogataea neopini* ATCC28781 strain, and the *Ogataea corticis* NBRC1794 strain.

(10) The yeast for ethanol production according to (8) or (9), wherein the microorganism corresponds to at least one strain selected from the group consisting of the *Ogataea dorogensis* NBRC101078 strain, the *Ogataea pini* ATCC76276 strain, the *Ogataea glucozyma* ATCC18938 strain, the *Ogataea neopini* ATCC28781 strain, and the *Ogataea corticis* NBRC1794 strain.

(11) The yeast for ethanol production according to (8) or (9), which has the ability to assimilate cellobiose.

(12) The yeast for ethanol production according to (11), which further has the ability to assimilate xylose.

In addition, *Ogataea dorogensis*, *Ogataea pini*, and *Ogataea glucozyma* are also known as *Pichia dorogensis*, *Pichia pini*, and *Pichia glucozyma*, respectively. Therefore, *Ogataea dorogensis*, *Ogataea pini*, and *Ogataea glucozyma* used herein include microorganisms identical to *Pichia dorogensis*, *Pichia pini*, and *Pichia glucozyma*, respectively.

Further, *Ogataea neopini* and *Ogataea corticis* correspond to a group of microorganisms previously classified as *Pichia pini* which, however, have been re-classified as differing from *Pichia pini* (=*Ogataea pini*).

Effects of the Invention

According to the ethanol production process of the present invention, ethanol can be produced in a medium containing cellobiose. Therefore, according to the ethanol production process of the present invention, ethanol can be produced at low cost without the need to use an enzyme that is necessary for degradation of cellobiose into glucose or a reaction system for such enzyme.

In addition, the present invention provides a yeast for ethanol production that has a novel function of synthesizing ethanol with the use of a cellobiose as a substrate and thus can be used for ethanol production.

This description includes part or all of the contents as disclosed in the description and/or drawings of Japanese Patent Application No. 2007-310870, which is a priority document of the present application.

BRIEF DESCRIPTION OF THE DRAWINGS

FIG. 1 shows a phylogenetic tree created based on the 26s rDNA-D1/D2 nucleotide sequences for yeasts, including the *Ogataea pini* ATCC76276 strain, the *Ogataea neopini* ATCC28781 strain, the *Ogataea corticis* NBRC1794 strain, the *Ogataea glucozyma* ATCC18938 strain, and the *Ogataea dorogensis* NBRC101078 strain.

BEST MODE FOR CARRYING OUT THE INVENTION

Hereinafter, the present invention is described in detail. In the ethanol production process of the present invention, a microorganism classified as a species selected from the group consisting of *Ogataea dorogensis, Ogataea pini, Ogataea glucozyma, Ogataea neopini,* and *Ogataea corticis* is used. As a microorganism belonging to *Ogataea dorogensis*, it is preferable to use the *Ogataea dorogensis* NBRC101078 strain. As a microorganism belonging to *Ogataea pini*, it is preferable to use the *Ogataea pini* ATCC76276 strain. As a microorganism belonging to *Ogataea glucozyma*, it is preferable to use the *Ogataea glucozyma* ATCC18938 strain. As a microorganism belonging to *Ogataea neopini*, it is preferable to use the *Ogataea neopini* ATCC28781 strain. As a microorganism belonging to *Ogataea corticis*, it is preferable to use the *Ogataea corticis* NBRC1794 strain. Also, it is possible define a microorganism that can be used for the ethanol production process of the present invention as a microorganism having 26s rDNA-D1/D2 comprising a nucleotide sequence having at least 97%, preferably at least 98%, and more preferably at least 99% homology with the nucleotide sequence of 26s rDNA-D1/D2 of any of the above strains. As described in the Examples below, the strains herein described have been found to have a novel function of producing ethanol with the use of cellobiose as a substrate. Specifically, a microorganism that can be used in the present invention is a microorganism belonging to any of the above species and having the ability to assimilate cellobiose. In addition, a microorganism that can be used in the present invention is preferably a microorganism of any of the above strains and having the ability to assimilate cellobiose.

Herein, among the above strains, the strains specified by their ATCC numbers have been deposited in the American Type Culture Collection. Those skilled in the art can purchase the strains according to prescribed procedures. In addition, among the above strains, the strains specified by NBRC numbers have been deposited in the NITE Biological Resource Center of the National Institute of Technology and Evaluation. Those skilled in the art can purchase the strains according to prescribed procedures.

In addition, in the ethanol production process of the present invention, one type of microorganism or a plurality of types of microorganisms selected from among the above microorganisms may be used.

Microorganisms that can be used in the ethanol production process of the present invention are not limited to the aforementioned strains provided from the ATCC or NRBC. Any strain can be used as long as it can be classified as corresponding to any of the above deposited strains. In other words, microorganisms that can be used in the ethanol production process of the present invention are not limited to microorganisms specified by the above deposition numbers and include microorganisms classified as corresponding to similar strains derived from the above strains. Such microorganisms derived from the above strains may be prepared by subjecting a provided original strain to treatment involving, for example, mutagenesis, or they may be isolated from a natural environment according to a general method.

Further, such microorganisms may be used as hosts for gene recombinants. That is to say, in the ethanol production process of the present invention, it is possible to use gene recombinants into which desired genes have been introduced with the use of the above microorganisms as hosts.

In the ethanol production process of the present invention, the above microorganisms are cultured in a medium containing cellobiose. Cellobiose used herein may be produced from cellulose contained in, for example, a woody biomass, with the use of cellobiohydrolase. Specifically, upon production of ethanol from a woody biomass, cellobiohydrolase is allowed to act on cellulose contained in a woody biomass so as to obtain cellobiose and then ethanol can be produced from cellobiose with the use of a microorganism described above.

Examples of a woody biomass used herein include, but are not particularly limited to, rice straw, rice husks, food waste, livestock excretion, woodchips, firewood, wood charcoal, chips, pellets, briquettes, lumbar chips, sawdust, tree bark, and construction debris. When cellulose contained in a woody biomass is formed into cellobiose, a cellobiohydrolase enzyme is allowed to act on cellulose or a microorganism that produces cellobiohydrolase can be used. Examples of a microorganisms that produces cellobiohydrolase include microorganisms belonging to the genus *Trichoderma* or the genus *Clostridium*. Also, when a cellobiohydrolase enzyme formulation is used, enzymes from microorganisms belonging to the genus *Trichoderma* or the genus *Clostridium* described above can be used.

Further, in the ethanol production process of the present invention, a medium composition is not particularly limited. A conventionally known medium composition can be used except that medium to be used contains cellobiose as a carbon source for ethanol production. In addition, it is possible to add a surfactant or a defoamant to a medium used for culture of a novel microorganism of the present invention depending on culture conditions and the like.

For instance, examples of carbon sources other than cellobiose include carbohydrates such as monosaccharide, disaccharide, oligosaccharide, and polysaccharide, and organic acid salts such as an acetate salt. As the carbon source used herein, it is possible to use each such component alone. Alternatively, if necessary, a mixture of a plurality of such components may be used. A specific example of a carbon source other than cellobiose is xylose. This is because a microorganism that can be used in the ethanol production process of the present invention is characterized by the ability to assimilate xylose, in addition to the ability to assimilate cellobiose. Further, examples of a nitrogen source include: inorganic and organic ammonium salts such as ammonia, ammonium chloride, ammonium sulfate, ammonium nitrate, ammonium carbonate, ammonium phosphate, and ammonium acetate; nitrogen-containing organic substances such as urea, peptone, meat extract, yeast extract, and casein hydrolysate; and amino acids such as glycine, glutamic acid, alanine, and methionine. As a nitrogen source used herein, it is possible to use each such component alone. Alternatively, if necessary, a mixture of a plurality of such components may be used. Moreover, examples of metal minerals include sodium chloride, ferrous sulfate, magnesium sulfate, manganese sulfate, zinc sulfate, and calcium carbonate. As a metal mineral used herein, it is possible to use each such component alone. Alternatively, if necessary, a mixture of a plurality of such components may be used.

In the ethanol production process of the present invention, culture conditions for culturing the aforementioned microorganisms are not particularly limited. Culture conditions can be adjusted to fall within the optimal pH and temperature ranges for growth of the above microorganisms. Specifically, the optimal pH range is 3 to 9, preferably 4 to 8, and more preferably 5 to 7. In addition, the optimal temperature range is 25° C. to 50° C., preferably 30° C. to 45° C., and more preferably 30° C. to 40° C. Culture may be either shaking culture with the use of a liquid medium or static culture with the use of a solid medium.

In particular, the concentration of cellobiose contained in a medium is not particularly limited. However, the concentration is 10% to 20%, preferably 5% to 10%, and more preferably 3% to 5%. Cellobiose may be added to a medium before culture or may be added during culture (feeding culture).

In the ethanol production process of the present invention, ethanol is collected from a medium. A process and an apparatus for collecting ethanol are not particularly limited. Any process or apparatus for collecting ethanol that is generally used for biomass ethanol production can be used. For example, ethanol contained in a medium can be collected by a process involving distillation or the use of an ethanol-permselective pervaporation membrane. The thus collected ethanol can be adequately purified in accordance with intended use.

EXAMPLES

The present invention is hereafter described in greater detail with reference to the following examples, although the technical scope of the present invention is not limited thereto.

Example 1

In this Example, 46 types yeast strains belonging to the genus *Pichia*, the genus *Candida*, the genus *Debaryomyces*, and the genus *Williopusis* were cultured in a medium containing cellobiose, followed by determination of the amounts of cellobiose and ethanol in the medium. In addition, the strains used herein were provided from the ATCC or NBRC.

In this Example, the medium used was prepared in a manner such that it contained cellobiose (Wako Pure Chemical Industries, Ltd.) (3.0%), peptone (Difco) (0.5%), a yeast extract (Difco) (0.3%), and a malt extract (Difco) (0.3%). First, each strain was precultured in a test tube containing a medium solution in an amount of 6 ml. For preculture, 1 platinum loop full of each strain was inoculated, the culture temperature was 30° C., the agitation rate was 120 rpm (amplitude: 40 mm), and the culture period was 1 day. After the completion of preculture, each strain was subjected to main culture with the use of a 500-mL baffled Erlenmeyer flask containing a medium solution in an amount of 100 ml. For main culture, the amount of strain inoculated was determined to be the amount at which OD=1 was achieved upon inoculation. For main culture, the culture temperature and the agitation rate were the same as those used for preculture. The period for main culture was 2 days.

The amount of cellobiose and the amount of ethanol were determined as follows. Specifically, two portions of the culture solution were aseptically collected from each flask during culture of a microorganism to be analyzed once daily, followed by determination of OD660 value, the ethanol concentration, and the cellobiose concentration. Each solution was diluted such that the OD660 value fell within the determination range. Absorption at a wavelength of 660 nm was determined by a spectrophotometer (Hitachi, Ltd., U-2000). The ethanol concentration and the cellobiose concentration were determined by HPLC. The HPLC conditions are described below.

In addition, for OD660 analysis, each sample was analyzed twice.

For HPLC, each sample was analyzed once.
  Column: Bio-rad HPX-87H
  Mobile layer: $0.005 NH_2SO_4$
  Flow rate: 0.6 ml/min
  Column temperature: 35° C.
  Detection: RI The ethanol yield was calculated for the 46 strains using the following equation. The ethanol yield was designated as the yield obtained based on a theoretical yield shown below.

$$\text{Yield based on a theoretical yield (\%)} = \frac{(\{\text{Maximum EtOH amount} - \text{Initital EtOH amount}\} \times 100)}{(\{\text{Initial amount of cellobiose} - \text{Remaining amount of cellobiose upon generation of EtOH at a maximum level}\} \times \text{Theoretical yield})}$$

Table 1 shows the ethanol yields calculated for the 46 examined strains.

TABLE 1

| | Species name in depositor | Strain No. | Remarks | Ethanol yield |
|---|---|---|---|---|
| 1 | *Pichia mississippiensis* | ATCC44357 | | 4.2 |
| 2 | *Pichia mississippiensis* | ATCC44358 | | 16.3 |
| 3 | *Pichia mississippiensis* | ATCC44360 | | 0 |
| 4 | *Pichia mississippiensis* | ATCC44361 | | 21.6 |
| 5 | *Pichia mississippiensis* | ATCC44362 | | 24.6 |
| 6 | *Pichia mississippiensis* | ATCC44363 | | 22.7 |
| 7 | *Pichia mississippiensis* | ATCC44364 | | 0 |
| 8 | *Pichia pini* | ATCC22693 | | 2.1 |
| 9 | *Pichia stipitis* | NBRC1687 | | 1.6 |
| 10 | *Pichia pini* | ATCC28780 | | 1.2 |
| 11 | *Pichia pini* | ATCC28781 | | 74.7 |
| 12 | *Pichia stipitis* | NBRC10006 | | 0 |
| 13 | *Pichia pini* | ATCC60373 | | 0 |
| 14 | *Pichia pini* | ATCC76276 | | 71.7 |
| 15 | *Candida salmanticensis* | NBRC10242 | | 23.1 |
| 16 | *Debaryomyces castellii* | NBRC1359 | | 16.9 |
| 17 | *Pichia euphorbiae* | NBRC10214 | | 27.2 |
| 18 | *Pichia euphorbiae* | NBRC100361 | | 29.8 |
| 19 | *Pichia meyerae* | NBRC10727 | | 36.8 |

TABLE 1-continued

| Species name in depositor | Strain No. | Remarks | Ethanol yield |
|---|---|---|---|
| 20 Pichia mississippiensis | NBRC10728 | | 7.6 |
| 21 Pichia pini | NBRC1342 | | 49.8 |
| 22 Pichia pini | NBRC1793 | | 24.2 |
| 23 Pichia pini | NBRC1794 | | 61.1 |
| 24 Pichia pini | NBRC1795 | | 14.7 |
| 25 Debaryomyces castellii | JCM6177 | | 6.7 |
| 26 Pichia pini | ATCC28779 | | 51.1 |
| 27 Pichia pini | ATCC28782 | | 51.7 |
| 28 Pichia glucozyma | ATCC18938 | | 68.6 |
| 29 Pichia henricii | ATCC18939 | | — |
| 30 Pichia henricii | ATCC60817 | | 65.6 |
| 31 Pichia zsoltii | NBRC101079 | | — |
| 32 Pichia glucozyma | NBRC1472 | ATCC18938 | 79.5 |
| 33 Pichia henricii | NBRC1477 | ATCC18939 | — |
| 34 Pichia henricii | NBRC1478 | | — |
| 35 Pichia pini | JCM3655 | | 40.4 |
| 36 Pichia henricii | JCM3611 | ATCC18939 | — |
| 37 Pichia henricii | JCM3612 | | — |
| 38 Pichia henricii | JCM3613 | NBRC1478 | — |
| 39 Candida nemodendra | ATCC36593 | | — |
| 40 Candida utilis | ATCC9255 | | — |
| 41 Pichia thermomethanolica | NBRC101504 | | 50.7 |
| 42 Candida nemodendra | NBRC10299 | ATCC36593 | 9.4 |
| 43 Williopsis salicorniae | NBRC10733 | | — |
| 44 Pichia dorogensis | NBRC101078 | | 63.7 |
| 45 Williopsis salicorniae | JCM10744 | NBRC10733 | — |
| 46 Candida nemodendra | JCM9855 | ATCC36593 | 9.6 |

As is understood from table 1, for the *Pichia pini* ATCC76276 strain, the *Pichia pini* ATCC28781 strain, the *Pichia pini* NBRC1794 strain, the *Pichia glucozyma* ATCC18938 strain, and the *Pichia dorogensis* NBRC101078 strain, the ethanol yield exceeded 60%. Therefore, such microorganisms were found to have a novel function of producing ethanol with the use of cellobiose as a substrate. In particular, for the *Pichia pini* ATCC76276 strain, the *Pichia pini* ATCC28781 strain, and the *Pichia glucozyma* ATCC18938 strain, the ethanol yield exceeded 70%, and thus they were found to be strains having particularly excellent ethanol synthesis capacity.

In addition, a 26s rDNA-D1/D2 nucleotide sequence was determined for each of the *Pichia pini* ATCC76276 strain, the *Pichia pini* ATCC28781 strain, the *Pichia pini* NBRC1794 strain, the *Pichia glucozyma* ATCC18938 strain, and the *Pichia dorogensis* NBRC101078 strain. Also, a 26s rDNA-D1/D2 nucleotide sequence was determined for each of the other strains. Then, a phylogenetic tree was created. The 26s rDNA-D1/D2 nucleotide sequences were determined as follows. Specifically, genomic DNA was first extracted from yeast with the use of a DNeasy Plant Mini Kit (QIAGEN). Next, PCR was carried out with the use of extracted genomic DNA as a template and puReTaq Ready-To-Go PCR beads (Amersham Biosciences) for amplification of the 26s rDNA-D1/D2 region. The following 4 types of primers were used for PCR.

```
NL1:
5'-GCATATCAATAAGCGGAGGAAAAG      (SEQ ID NO: 6)

NL2:
5'-CTCTCTTTTCAAAGTTCTTTTCATCT    (SEQ ID NO: 7)

NL3:
5'-AGATGAAAAGAACTTTGAAAAGAGAG    (SEQ ID NO: 8)

NL4:
5'-GGTCCGTGTT TCAAGACGG           (SEQ ID NO: 9)
```

Next, the nucleotide sequence of the amplified 26s rDNA-D1/D2 region was determined with the use of ABI PRISM 3100 Genetic Analyzer System (Applied Biosystems). SEQ ID NO: 1 represents the 26s rDNA-D1/D2 nucleotide sequence of the *Pichia pini* ATCC76276 strain. SEQ ID NO: 2 represents the 26s rDNA-D1/D2 nucleotide sequence of the *Pichia pini* ATCC28781 strain. SEQ ID NO: 3 represents the 26s rDNA-D1/D2 nucleotide sequence of the *Pichia pini* NBRC1794 strain. SEQ ID NO: 4 represents the 26s rDNA-D1/D2 nucleotide sequence of the *Pichia glucozyma* ATCC18938 strain. SEQ ID NO: 5 represents the 26s rDNA-D1/D2 nucleotide sequence of the *Pichia dorogensis* NBRC101078 strain. Based on the obtained nucleotide sequence information, homology search was conducted with the use of international nucleotide sequence databases (GenBank/DDBJ/EMBL).

FIG. 1 shows a phylogenetic tree created based on the analysis results described above. As a result of creation of the phylogenetic tree, it was revealed that a group of microorganisms that have been conventionally classified as members of the genus *Pichia* differ from those belonging to the genus *Pichia*, and therefore they can be re-classified as members of the genus *Ogataea*. In particular, it was found that the *Pichia pini* ATCC76276 strain, the *Pichia pini* ATCC28781 strain, the *Pichia pini* NBRC1794 strain, the *Pichia glucozyma* ATCC18938 strain, and the *Pichia dorogensis* NBRC101078 strain, which have been found to have a novel function of producing ethanol with the use of cellobiose as a substrate, can be classified as the *Ogataea pini* ATCC76276 strain, the *Ogataea neopini* ATCC28781 strain, the *Ogataea corticis* NBRC1794 strain, the *Ogataea glucozyma* ATCC18938 strain, and the *Ogataea dorogensis* NBRC101078 strain, respectively. The *Pichia pini* ATCC28781 strain (No. 11) and the *Pichia pini* NBRC1794 strain (No. 23), which were found to be excellent in terms of the ethanol yield, are not classified as *Ogataea pini* strains. The strains were found to correspond to new species. Therefore, it was concluded that they correspond to the *Ogataea neopini* ATCC28781 strain and the *Ogataea corticis* NBRC1794 strain, respectively.

The above results indicate that microorganisms selected from among microorganisms belonging to *Ogataea dorogensis*, microorganisms belonging to *Ogataea pini*, microorganisms belonging to *Ogataea glucozyma*, microorganisms belonging to *Ogataea neopini*, and microorganisms belonging to *Ogataea corticis* have an excellent function of synthesizing ethanol from cellobiose.

All publications, patents, and patent applications cited herein are incorporated herein by reference in their entirety.

The invention claimed is:

1. An ethanol production process, comprising the steps of: culturing a microorganism selected from the group consisting of the *Ogataea dorogensis* NBRC101078 strain, the *Ogataea pini* ATCC76276 strain, the *Ogataea neopini* ATCC28781 strain, and the *Ogataea corticis* NBRC 1794 in a medium containing cellobiose; and collecting ethanol from the medium.

2. The ethanol production process according to claim 1, wherein the cellobiose is derived from cellulose contained in a woody biomass.

3. The ethanol production process according to claim 2, which further comprises a step of degrading the cellulose contained in a woody biomass into cellobiohydrolase.

4. The ethanol production process according to claim 1, wherein the microorganism has the ability to assimilate cellobiose.

5. The ethanol production process according to claim 4, wherein the microorganism further has the ability to assimilate xylose.

* * * * *